(12) United States Patent
Mattingly et al.

(10) Patent No.: US 7,037,494 B2
(45) Date of Patent: May 2, 2006

(54) FORMULATIONS AND METHODS FOR INSECT CONTROL

(75) Inventors: Stephen J. Mattingly, San Antonio, TX (US); David L. Johnson, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 10/074,700

(22) Filed: Feb. 13, 2002

(65) Prior Publication Data

US 2003/0068304 A1    Apr. 10, 2003

Related U.S. Application Data

(63) Continuation-in-part of application No. 09/951,833, filed on Sep. 11, 2001, which is a continuation of application No. 09/529,581, filed as application No. PCT/US98/21511 on Oct. 13, 1998, now abandoned.

(60) Provisional application No. 60/061,841, filed on Oct. 14, 1997.

(51) Int. Cl.
A01N 63/00     (2006.01)
A01N 25/08     (2006.01)

(52) U.S. Cl. ..................... 424/93.4; 424/410

(58) Field of Classification Search ................ 435/410, 435/93.4
See application file for complete search history.

(56) References Cited

U.S. PATENT DOCUMENTS

| | | | |
|---|---|---|---|
| 3,642,982 A * | 2/1972 | Morimoto et al. | |
| 4,421,759 A | 12/1983 | Boisvenue | 424/273 |
| 4,460,606 A | 7/1984 | Bettarini et al. | 424/341 |
| 4,540,711 A | 9/1985 | Bettarini | 514/720 |
| 4,925,663 A | 5/1990 | Stimac | 424/93 |
| 4,983,390 A | 1/1991 | Levy | 424/404 |
| 4,992,275 A | 2/1991 | Lush | 424/408 |
| 5,364,618 A | 11/1994 | Meer et al. | 424/84 |
| 5,366,892 A * | 11/1994 | Foncerrada et al. | |
| 5,413,784 A | 5/1995 | Wright et al. | 424/93.5 |
| 5,427,786 A * | 6/1995 | Payne et al. | |
| 5,453,277 A | 9/1995 | McCoy | 424/408 |
| 5,480,638 A | 1/1996 | Erwin | 424/84 |
| 5,516,513 A | 5/1996 | Wright | 424/93.3 |
| 5,523,083 A * | 6/1996 | Shasha et al. | |
| 5,683,689 A | 11/1997 | Stimac et al. | 424/93.5 |
| 5,837,273 A | 11/1998 | Shasha et al. | 424/405 |
| 5,850,707 A | 12/1998 | Fell et al. | 43/131 |
| 5,997,945 A | 12/1999 | Shasha et al. | 427/213.3 |

FOREIGN PATENT DOCUMENTS

| | | | |
|---|---|---|---|
| JP | 60027672 | * | 2/1985 |
| JP | 05247378 | * | 9/1993 |
| JP | 05304959 | * | 11/1993 |
| JP | 09238681 | * | 9/1997 |
| KR | 9411524 | * | 10/1991 |

OTHER PUBLICATIONS

Methods in Biotechnology, vol. 5 : Biopesticides:Use and Delivery. F.R. Hall and J.J. Menn, eds. Humana Press, Totowa, NJ Chapter 1, Biopesticides: Present Status and Future Prospects. Julius J. Menn and Franklin R. Hall.pp. 1-10.

Methods in Biotechnology, vol 5: Biopesticides : Use and Delivery. Edited by F.R. Hall and J.J. Menn. Humana Press, Inc. Totowa, NJ. Chapter 3, Microbial Biopesticides: the European Scence. Editors: Tariq M. Butt, John G. Harris, and Keith A. Powell.pp 23-45.

From Methods in Biotechnology, vol. 5 : Biopesticides: Use and Delivery. Edited by: F.R. Hall and J.J. Menn Humana Press, Inc. Totowa, NJ Chapter 14. Editors: Stephen P. Wright and Raymond I. Carruthers. Production, Delivery, and Use of Mycoinsecticides for Control of Insect Pests on Field Crops. pp. 233-269.

(Continued)

Primary Examiner—Christopher R. Tate
(74) Attorney, Agent, or Firm—Robert W. Strozier

(57) ABSTRACT

A composition is disclosed from controlling an insect population including an insect food stuff and an insecticidally effective amount of at least one Gram negative bacteria, viable, dead or alive, and/or an extract thereof, where the composition is applied to an area accessible to the insects and results in insect death. The compositions are ideally suited for the control of fire ants, cockroaches, carpenter ants and termites. For fire ant and cockroach control, the food stuff is a carbohydrate rich material, while for carpenter ant and termite control, the food stuff is a cellulosic rich material. The composition is applied to the area as a single treatment or as a periodic treatment in an amount have from about $5 \times 10^9$ to about $1 \times 10^{13}$ bacteria or extracts from that number of bacteria.

17 Claims, No Drawings

OTHER PUBLICATIONS

From Methods in Biotechnology, vol. 5 : Biopesticides: Use and Delivery. Edited by: F. R.Hall and J.J. Menn. Humana Press Inc. Totowa , NJ Chapter 11: Fermentation-Derived Insect Control Agents: the Spinosyns.Edited by : Thomas C. Sparks, Gary D. Thompson, Herbert A. Kirst, Mark B.Hertlein, Jon S. Mynderse, Jan R. Turner, and Thomas V. Worden. pp. 171-188.

From : Methods in Biotechnology, vol. 5: Biopesticides: Use and Delivery. Edited By F. R. Hall and J. J. Menn. Humana Press, Inc Totowa, NJ. Chapter 5: Pesticide Policy Influences on Biopesticides Technologies. Edited by Noel D. Uri. pp. 55-73.

From : Methods in Biotechnology, vol. 5 : Biopesticides: Use and Delivery. Edited by: F.R. Hall and J.J. Menn. Humana Press, Inc. Totowa, NJ. Chapter 15: Entomopathogenic Nematodes. Edited by Parwinder Grewal and Ramon Georgis. pp. 271-299.

From: Methods in Biotechnology, vol. 5: Biopesticides: Use and Delivery. Edited by: F.R. Hall and J.J. Menn. Humana Press, Inc. Totowa, NJ. Chapter 16: Naturally Occurring Baculoviruses for Insect Pest Control. Edited by Brian A. Federici . pp. 301-321.

From: Methods in Biotechnology, vol. 5: Biopesticides: Use and Delivery. Edited by: F.R. Hall and J. J. Menn. Humana Press, Inc. Totowa, NJ. Chapter 22: The Federal Registration Process and Requirements for the United States. Edited by J. Thomas McClintock. pp. 415-441.

Tektran. United State Department of Agriculture . Agricultural Research Service. A Strain of Serratia Marcescens with High Virulence Per OS to the Corn Earworm. Authors: Farrar, Robert R. and Martin, Phyllis A. and Ridgway, Richard L. Website: www.nalusda.gov pp. 1 of 2.

EPA. United States Environmental Protection Agency. Office of Pesticide Programs. Biopesticides. Website: www.epa.gov/pesticides/biopesticides/index.html. Nov. 12, 1999.

Mississippi State University Extension Service . The Imported Fire Ant and ITS Control. pp. 1-5. Website: ww.ext.msstate.edu/pubs/pub1833.html.

Fire Ants by the Dirt Doctor. Howard Garrett. Organic Manual. 1996. pp. 1-3.

Chapter 27: Diseases of Fire Ants: Problems and Opportunities. Author: D.P. Jouvenaz. pp. 327-338. From: Control Strategies I.

* cited by examiner

FORMULATIONS AND METHODS FOR INSECT CONTROL

RELATED APPLICATIONS

This application is a Continuation-In-Part of co-pending U.S. patent application Ser. No. 09/951,833 filed Sep. 11, 2001, which is a continuation of U.S. patent application Ser. No. 09/529,581 filed Apr. 14, 2000, abandoned, which is a nationalized from PCT Application Ser. No. PCT/US98/21511, filed Oct. 13, 1998, which claimed provisional priority to U.S. Provisional Patent Application Ser. No. 60/061,841, filed Oct 14, 1997.

BACKGROUND OF THE INVENTION

1. Field of the Invention

The present invention relates to a composition for controlling insect populations including an effective insecticidal amount of a viable Gram negative bacteria, a dead Gram negative bacteria, an extract of a Gram negative bacteria or a mixture or combination thereof and method for making and using same.

More particularly, the present invention relates to a dry composition for controlling insect populations including an insect food stuff and an effective insecticidal amount of a viable Gram negative bacteria, a dead Gram negative bacteria, an extract of a Gram negative bacteria or a mixture or combination thereof and method for making and using same.

2. Description of the Related Art

The red imported fire ant, *Solenopsis invicta*, was accidently imported from South America into the United States in the 1930s. During the intervening time period, it has spread throughout the southern states and Puerto Rico and is estimated to infest over 150 million hectares (Lofgren, 1986a). Its high population density correlates with man's activities, which has made it one of the most significant health and agricultural pest ant species (Adams, 1986). Its potent sting and injected alkaloid venom has resulted in a larger number of hypersensitivity reactions than seen with bee stings (Adams and Lofgren, 1981). Its effect on agricultural production of a variety of crops including soybeans, potatoes, corn, citrus, okra and others is well known (Vander Meer, 1986). The preferred diet of the adult red imported fire ant appears to be carbohydrate (Vander Meer et al., 1995).

Attempts to control the red imported fire ants have included extensive use of several approaches: persistent chlorinated hydrocarbon insecticides (Adams, 1986); vegetable oil phagostimulant/active ingredient solvent (Banks et al., 1985); subterranean fogging devices (Amdro Fire Ant Insecticide, 1987); Amdro®, containing a chemical-based insecticide (Logic Fire Ant Bait, technical data, commercial brochure), and Logic®, containing fenoxycarb, a growth regulator, which when ingested by the queen prevents the development of eggs that would normally develop into worker ants (Logic Professional Fire Ant Bait, product label, Te,inix International, Inc.). In Texas attempts are underway to used phorid flies in the biocontrol of imported fire ants (L.E. Gilbert Laboratory, U. T. Austin, 1997). As far as the inventors are aware, there are no microbial-based formulations to control the fire ant population.

The control of insect pests, particularly in environmentally safe manner is a perennial problem. For reasons of health and aesthetics, it is desirable to control insect populations. Imported red fire ants (*Solenopsis invicta* and other strains) have proven to be pests and potential health risks in many parts of this country. Biologically safe methods for control of fire ants and other insects have been less than completely satisfactory. The avermectin- producing *Streptomyces avermitilis* has been used to produce avermectin which was thought to be usable in the control of fire ant population.

Other chemical insecticides have been used in attempts to, suppress insect pests. Various other suppression or eradication systems have been tested and yet insect control, as exemplified by the imported fire ant problem remains unsolved, despite the use of various insecticides.

Thus, there is a need in the art for more environmentally friendly control formulation for fire ants and other common insects based on a bait containing either viable or/and dead microbes, extracts thereof and/or mixtures thereof.

SUMMARY OF THE INVENTION

Microbial Compositions

The present invention provides a composition for controlling an insect population including an insecticidal amount of: a viable microorganism, a dead microoganism, a microorganism extract or a mixture or combination thereof, where the microorganism, viable, inviable, dead or alive, or the extract, is deleterious to an insect population or when ingested by an insect, results in insect death.

The present invention provides a composition for controlling an insect population including an insecticidal amount of: a plurality of species of viable microorganisms, a plurality of species of dead microorganisms, extracts from a plurality of species of microorganisms, or mixtures or combinations thereof, where each species of microorganisms, alive or dead, or extracts thereof, is deleterious to an insect population or when ingested by an insect, results in insect death.

The present invention provides a composition for controlling an insect population including an insecticidal amount of: a viable Gram negative bacteria, a dead Gram negative bacteria, an extract of a Gram negative bacteria, or a mixture or combination thereof, where the Gram negative bacteria, alive or dead, or the extract, is deleterious to an insect population or when ingested by an insect, results in insect death.

The present invention provides a composition for controlling an insect population including an insecticidal amount of: a plurality of species of viable Gram negative bacteria, a plurality of species of dead Gram negative bacteria, extracts from a plurality of species of Gram negative bacteria, or mixtures or combinations thereof, where each species of Gram negative bacteria, alive or dead, or extracts thereof, is deleterious to an insect population or when ingested by an insect, results in insect death.

The present invention provides a composition for controlling an insect population including at least one Gram negative bacteria from the Proteobacteria phylum.

The present invention provides a composition for controlling an insect population including at least one Gram negative bacteria selected from the group consisting of: Purple Phototrophic Bacteria; Nitrifying Bacteria; Sulfur- and Iron-Oxidizing Bacteria; Hydrogen-Oxidizing Bacteria, Methanotrophs and Methyltrophs, *Pseudomonas* and the *Pseudomonads*, Acetic Acid Bacteria (Acetobacteraceae), Free-Living Aerobic Nitrogen-Fixing Bacteria, *Neisseria*, Chromobacterium, and Relatives, Enteric Bacteria, *Vibrio* and Photobacterium, Rickettsias, Spirilla, Sheathed Proteobacteria, Budding and Prosthecate/Stalked Bacteria, Gliding Myxoacteria, Sulfate- and Sulfur-Reducing Bacteria, enterobacteriaceae including *Escherichia coli, Shigella*, Edwardsiella, *Salmonella, Citrobacter, Klebsiella, Enterobacter, Serratia, Proteus, Morganella, Poridincia, Yersiria* and mixtures or combinations thereof.

The present invention provides a composition for controlling an insect population including a food stuff and at least one bacteria selected from the group consisting of Purple Phototrophic Bacteria, *Pseudomonas* and the Pseudomonads, Enteric Bacteria and mixtures or combinations thereof.

The present invention provides a composition for controlling an insect population including an insect food and at least one Gram negative bacteria from the Proteobacteria family that has low or no human pathology.

The present invention provides a composition for controlling an insect population including an insect food and at least one Gram negative bacteria from the genus Rhodobacter.

The present invention provides a composition for controlling an insect population including an insecticidal amount of: a Gram negative bacteria or extract thereof, where the Gram negative bacteria are selected from genera consisting of *Pseudomonas, Enterobacter, Serratia, Rhodobacter*, or mixtures or combination thereof, where each Gram negative bacteria, alive or dead, or extracts thereof, is deleterious to an insect population or when ingested by an insect, results in insect death.

The present invention provides a composition for controlling an insect population including an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Compositions of Microbes and Insect Food Stuff

The present invention provides a composition for controlling an insect population including an insect food stuff and an insecticidal amount of: a viable microorganism, a dead microoganism, a microorganism extract or a mixture or combination thereof, where the microorganism, dead or alive, or the extract, is deleterious to an insect population or when ingested by an insect, results in insect death.

The present invention provides a composition for controlling an insect population including an insect food stuff and an insecticidal amount of: a plurality of species of viable microorganisms, a plurality of species of dead microorganisms, extracts from a plurality of species of microorganisms, or mixtures or combinations thereof, where each species of microorganisms, alive or dead, or extracts thereof, is deleterious to an insect population or when ingested by an insect, results in insect death.

The present invention provides a composition for controlling an insect population including an insect food stuff and an insecticidal amount of: a viable Gram negative bacteria, a dead Gram negative bacteria, an extract of a Gram negative bacteria, or a mixture or combination thereof, where the Gram negative bacteria, alive or dead, or the extract, is deleterious to an insect population or when ingested by an insect, results in insect death.

The present invention provides a composition for controlling an insect population including an insect food stuff and an insecticidal amount of: a plurality of species of viable Gram negative bacteria, a plurality of species of dead Gram negative bacteria, extracts from a plurality of species of Gram negative bacteria, or mixtures or combinations thereof, where each species of Gram negative bacteria, alive or dead, or extracts thereof, is deleterious to an insect population or when ingested by an insect, results in insect death.

The present invention provides a composition for controlling an insect population including an insect food stuff and an insecticidal amount of: a Gram negative bacteria or extract thereof, where the Gram negative bacteria are selected from genera consisting of *Pseudomonas, Enterobacter, Serratia, Rhodobacter*, or mixtures or combination thereof, where each Gram negative bacteria, alive or dead, or extracts thereof, is deleterious to an insect population or when ingested by an insect, results in insect death.

The present invention provides a composition for controlling an insect population including an insect food stuff and an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Baits

The present invention provides a bait for controlling an insect population including an insect food stuff and an insecticidal amount of: a viable microorganism, a dead microorganism, a microorganism extract or a mixture or combination thereof, where the microorganism, dead or alive, or the extract, is deleterious to an insect population or when ingested by an insect, results in insect death.

The present invention provides a bait for controlling an insect population including an insect food stuff and an insecticidal amount of: a plurality of species of viable microorganisms, a plurality of species of dead microorganisms, extracts from a plurality of species of microorganisms, or mixtures or combinations thereof, where each species of microorganisms, alive or dead, or extracts thereof, is deleterious to an insect population or when ingested by an insect, results in insect death.

The present invention provides a bait for controlling an insect population including an insect food stuff and an insecticidal amount of: a viable Gram negative bacteria, a dead Gram negative bacteria, an extract of a Gram negative bacteria, or a mixture or combination thereof, where the Gram negative bacteria, alive or dead, or the extract, is deleterious to an insect population or when ingested by an insect, results in insect death.

The present invention provides a bait for controlling an insect population including an insect food stuff and an insecticidal amount of: a plurality of species of viable Gram negative bacteria, a plurality of species of dead Gram negative bacteria, extracts from a plurality of species of Gram negative bacteria, or mixtures or combinations thereof, where each species of Gram negative bacteria, alive or dead, or extracts thereof, is deleterious to an insect population or when ingested by an insect, results in insect death.

The present invention provides a bait for controlling an insect population including an insect food stuff and an insecticidal amount of: a Gram negative bacteria or extract thereof, where the Gram negative bacteria are selected from genera consisting of *Pseudomonas, Enterobacter, Serratia,*

*Rhodobacter*, or mixtures or combination thereof, where each Gram negative bacteria, alive or dead, or extracts thereof, is deleterious to an insect population or when ingested by an insect, results in insect death.

The present invention provides a bait for controlling an insect population including an insect food stuff and an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Fire Ant Bait

The present invention provides a bait for controlling fire ant populations including an insect food stuff comprising a carbohydrate and an insecticidal amount of: a Gram negative bacteria or extract thereof, where the Gram negative bacteria are selected from genera consisting of *Pseudomonas, Enterobacter, Serratia, Rhodobacter*, or mixtures or combination thereof, where each Gram negative bacteria, alive or dead, or extracts thereof, is deleterious to an insect population or when ingested by an insect, results in insect death.

The present invention provides a bait for controlling an insect population including an insect food stuff comprising a carbohydrate and an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Cockroach Bait

The present invention provides a bait for controlling fire ant populations including an insect food stuff comprising a carbohydrate and an insecticidal amount of: a Gram negative bacteria or extract thereof, where the Gram negative bacteria are selected from genera consisting of *Pseudomonas, Enterobacter, Serratia, Rhodobacter*, or mixtures or combination thereof, where each Gram negative bacteria, alive or dead, or extracts thereof, is deleterious to an insect population or when ingested by an insect, results in insect death.

The present invention provides a bait for controlling an insect population including an insect food stuff comprising a carbohydrate and an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Carpenter Ant Bait

The present invention provides a bait for controlling fire ant populations including an insect food stuff comprising a cellulose material and an insecticidal amount of: a Gram negative bacteria or extract thereof, where the Gram negative bacteria are selected from genera consisting of *Pseudomonas, Enterobacter, Serratia, Rhodobacter*, or mixtures or combination thereof, where each Gram negative bacteria, alive or dead, or extracts thereof, is deleterious to an insect population or when ingested by an insect, results in insect death.

The present invention provides a bait for controlling an insect population including an insect food stuff comprising a cellulose material and an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Termite Bait

The present invention provides a bait for controlling fire ant populations including an insect food stuff comprising a cellulose material and an insecticidal amount of: a Gram negative bacteria or extract thereof, where the Gram negative bacteria are selected from genera consisting of *Pseudomonas, Enterobacter, Serratia, Rhodobacter*, or mixtures or combination thereof, where each Gram negative bacteria, alive or dead, or extracts thereof, is deleterious to an insect population or when ingested by an insect, results in insect death.

The present invention provides a bait for controlling an insect population including an insect food stuff comprising a cellulose material and an insecticidal amount of: a Gram negative bacteria or extract thereof, where the Gram negative bacteria are selected from groups consisting of *Pseudomonas aeruginosa, Enterobacter agglomerans, Enterobacter aerogenes, Serratia marcescens, Rhodobacter capsulatus*, or mixtures or combinations thereof, where each Gram negative bacteria, alive or dead, or extracts thereof, is deleterious to an insect population or when ingested by an insect, results in insect death.

Methods for Insect Control

The present invention provides a method for controlling insect populations including the step of applying, in proximity to an insect colony, a sufficient amount of a composition of this invention to result in the death of the colony.

The present invention provides a method for controlling insect populations including the steps of applying, in proximity to an insect colony, a first amount of a composition of this invention sufficient to result in the death of the colony and applying, in proximity to an insect colony, a second amount of a composition of this invention sufficient to ensure the death of the colony and to prevent colony reestablishment.

The present invention provides a method for controlling insect populations including the step of periodically applying, in proximity to an insect colony, an amount of a composition of this invention to result in the death of the colony and to prevent the establishment of new colonies.

The present invention provides a method for controlling insect populations including the step of applying to an area of land an amount of a composition of this invention sufficient to result in the death of insect colonies on the area of land.

The present invention provides a method for controlling insect populations including the step of periodically applying to an area of land an amount of a composition of this invention sufficient to result in the death of insect colonies on the area of land and to prevent the establishment of new colonies.

The present invention provides a method for effectively administering population-controlling materials to a fire ant colony. The method involves preparing a dried particulate mixture comprising a carbohydrate and at least one preferably viable fire ant population-controlling microbe as a bacterial pesticide. The mixture is then applied in proximity to a fire ant mound or made available in the area patrolled by the insect. In one preferred embodiment, the carbohydrate is included in a cereal bran. One effective cereal bran is oat bran. The carbohydrate may also include dried milk and to a residue of a thioglycollate bacterial broth. A preferable bacterial pesticide is at least one of a *Pseudomonas aeruginosa, Enterobacter agglomerans, Enterobacter aerogenes, Serratia marcescens*, and *Rhodobacter capsulatus*, and mixtures or combination thereof.

The present invention provides a method for administering an effective application of isolated strains of *Pseudomonas aeruginosa, Enterobacter agglomerans, Enterobacter aerogenes* and *Serratia marcescens* to fire ant colonies. The bacterial strains are preferably contained on carbohydrate-rich particles that are retrieved and ingested by the ants. Subsequent to an effective application, fire ant colonies were found to become abandoned and contain only dead ants.

This method comprises preparing or obtaining a particulate mixture comprising a carbohydrate and a possible insect population depletor, such as a bacterial insecticide. An effective amount of the mixture is applied to an area populated by insects. The insects consume the material and/or retrieve it for consumption by other insects. A preferred particulate mixture comprises a cereal bran. In a preferred method the agent insecticide or pathogen is a bacterium. In another preferred method the agent is at least one of *Pseudomonas aeruginosa, Enterobacter aerogenes, Enterobacter agglomerans*, and *Serratia marcescens* most preferably isolated from commercial grease traps. These methods appear to be effective for many insects, including cockroaches, carpenter ants, fire ants, and termites.

The particulate material should include an appropriate "bait" to induce consumption by target insects. For example, the carbohydrate in oat bran and/or dried-milk thioglycollate bacterial broth residue with is an effective "bait" for fire ants and cockroaches. It is envisioned that cellulose would attract termites and that other insects would be attracted by the same or other dietary components or flavorings.

Extracts of Gram Negative Bacteria

The present invention also relates to extracts of Gram negative bacteria which are insecticides of insects including fire ants, cockroaches, carpenter ants, termites or other insects. The extracts of the present invention include dehydrated bacteria which are non-viable, ruptured, dehydrated bacterial materials, and any other extract of a Gram negative bacteria that includes materials insecticidal to insects including endotoxins produced by the Gram negative bacteria and especially the lipopolysaccharide endotoxins produced by the Gram negative bacteria.

DETAILED DESCRIPTION OF THE INVENTION

The inventors have found that an insecticidal bait can be prepared for the control of insect populations, where the bait includes viable and/or non-viable Gram negative bacteria and/or an extract of a Gram negative bacteria. Preferably, the bait also include a insect food stuff, which is tailored to the specific insect being controlled. For fire ants and cockroaches, the preferred food stuff is a material rich in carbohydrates such as a cereal bran or, of course, any purified carbohydrate. For termites and carpenter ants, the preferred food stuff is a material rich in cellulose, such as saw dust or any purified cellulosic material. The inventors have found that a single application of the compositions of this invention to an area accessible to the insect to be controlled can result in partial to complete insect eradication. Of course, repeated application will ensure that re-infestation does not occur. For fire ant control, it is preferred to periodically apply the composition of the present invention at the recommended dosage to any area one desires to keep relatively insect free. By an area accessible to the insects to be controlled, the inventors mean an place were the insects will find the composition and either ingest it and/or take to its nest for subsequent ingestion.

Broadly, the present invention relates to an insecticide including at least one species of bacteria from the family Proteobacteria. More particularly, the insecticide includes at least one Gram negative bacteria selected from the group consisting of: Purple Phototrophic Bacteria; Nitrifying Bacteria; Sulfur- and Iron-Oxidizing Bacteria; Hydrogen-Oxidizing Bacteria, Methanotrophs and Methyltrophs, *Pseudomonas* and the Pseudomonads, Acetic Acid Bacteria (Acetobacteraceae), Free-Living Aerobic Nitrogen-Fixing Bacteria, *Neisseria*, Chromobacterium, and Relatives, Enteric Bacteria, *Vibrio* and Photobacterium, Rickettsias, Spirilla, Sheathed Proteobacteria, Budding and Prosthecate/ Stalked Bacteria, Gliding Myxoacteria, Sulfate- and Sulfur-Reducing Bacteria and mixtures or combinations thereof. More specifically, the insecticide includes a food stuff and at least one bacteria selected from the group consisting of Purple Phototrophic Bacteria, *Pseudomonas* and the Pseudomonads, Enteric Bacteria and mixtures or combinations thereof Most specifically, the insecticide includes an insect food and at least one Gram negative bacteria from the Proteobacteria family that has low or no human pathology, especially from the genus *Rhodobacter*.

The present invention provides an oat bran-dried milk particulate mixture containing a bacterial pesticide such as one or more of a viable Gram negative organism, e.g. *Pseudomonas, Enterobacter* and *Serratia marcescens* has been found to eliminate or decrease populations of cockroaches and other insects. With an appropriate bait formulation containing bacteria, insects, including carpenter ants, termites and fire ants of any variety, can be controlled. Termite bait of course would preferably involve a cellulosic material. Carpenter ants may be baited more properly by a particulate mixture comprising, for example, peanut extract (peanut butter or the like). An important aspect of the present invention is including an appropriate bacterial pesticide with insect food. The pesticide is preferably slow-acting, not killing the insects immediately.

The present invention involves finding a biologically safe and effective method to control undesired insect populations and the spread of pests such as imported red fire ants. Generally the insect bait of the present invention may be prepared as follows: bacterial pesticides, including *Pseudomonas aeruginosa, Enterobacter aerogenes, Enterobacter agglomerans* and *Serratia marcescens*, are grown individually in bacterial media to log phase or, preferably, stationary phase. The bacteria are removed from the bacterial media by centrifugation, filtration or any other means known to those of skill in the art. The bacteria are then resuspended in a medium comprising skim milk and/or other appropriate suspension media such as thioglycollate medium. Dry oat bran or some other attractive food source for insects is then added to the bacterial suspension. The materials are mixed thoroughly and then lyophilized or otherwise dried without significantly damaging bacteria viability. Following lyophilization or drying, the dry material is weighed and is ready for use. It is believed that the bacteria used in the methods described are entirely safe to humans and animals. Preferably, for treatment of fire ant mounds, a quantity of bait containing from about $5 \times 10^9$ to about $1 \times 10^{13}$ bacteria is applied to each mound, where the bacteria are either viable, inviable or a mixture or combination thereof. In this invention, mixtures of different bacterial species and/or strains or a single bacterial species and/or strain may be ultimately combined with an insect food stuff to form a bait. For fire ants, a carbohydrate-rich bait in a dry state for broadcast in the area or application to fire ant mounds. The carbohydrate-rich food stuff is a food stuff including at least 60 wt. % carbohydrate.

The present invention broadly involves a method for controlling insect populations.

The present invention provides a dry particulate mixture comprising an insect food stuff and an insecticidal effective amount of a microbe, an extract thereof or a mixture or combination thereof, where the microbe, dead, alive, inviable or viable, or the exact or the mixture or combination is deleterious to an insect population. The mixture is ideally suited for the control of fire ant populations. In certain formulations, the bacteria is most preferably viable and, in an important embodiment, at least one of *Pseudomonas aeruginosa, Enterobacter agglomerans, Enterobacter aerogenes, Serratia marcescens*, or mixtures or combinations thereof A cereal bran containing carbohydrate milk solid and thioglycollate medium solids have been found particularly beneficial in both attracting insect consumption and stabilizing viable bacteria. In certain formulations, the bacteria can be alive or dead, viable or non-viable, and, in an important embodiment, the formulations include dead bacteria from at least one species of the genus *Rhodobacter* or mixture of species from the genus *Rhodobacter*, and for fire ant population, the food stuff is a carbohydrate, especially oat bran. In a most preferred formulation of dead or alive bacteria, *Rhodobacter capsulatus* is the bacteria, which has no known human pathology.

The present invention provides an oat bran-dried milk particulate mixture containing a bacterial pesticide such as one or more of a viable Gram negative organism, e.g. *Pseudomonas, Enterobacter* and *Serratia marcescens* has been found to eliminate or decrease populations of cockroaches and other insects. With an appropriate bait formulation containing bacteria, insects, including carpenter ants, termites and fire ants of any variety, can be controlled. Termite bait of course would preferably involve a cellulosic material. Carpenter ants may be baited more properly by a particulate mixture comprising, for example, peanut extract (peanut butter or the like). An important aspect of the present invention is including an appropriate bacterial pesticide with insect food. The pesticide is preferably slow-acting, not killing the insects immediately.

Suitable Gram negative bacteria for the practice of this invention include, without limitation, Gram negative bacteria from the Kingdom Proteobacteria. Suitable Gram negative bacteria from the Kingdom Proteobacteria include, without limitation: Purple Phototrophic Bacteria; Nitrifying Bacteria; Sulfur- and Iron-Oxidizing Bacteria; Hydrogen-Oxidizing Bacteria, Methanotrophs and Methyltrophs, *Pseudomonas* and the Pseudomonads, Acetic Acid Bacteria (Acetobacteraceae), Free-Living Aerobic Nitrogen-Fixing Bacteria, *Neisseria*, Chromobacterium, and Relatives, Enteric Bacteria, *Vibrio* and Photobacterium, Rickettsias, *Spirilla*, Sheathed Proteobacteria, Budding and Prosthecate/Stalked Bacteria, Gliding Myxoacteria, and Sulfate- and Sulfur-Reducing Bacteria.

Purple Phototrophic Bacteria include: purple sulfur bacteria such as bacteria from the genera Chromatium, Halorhodospira, Thiocapsa, Thiococcus, Thiopedia, and Thiospirillum, which are photolithoautotrophs and often form sulfur granules inside their cells; and purple nonsulfur bacteria such as bacteria from the genera *Rhodobacter, Rhodocyclus, Rhodobacter, Rhodopseudomonas*, and *Rhodophila*, which are photoorganotrophs and found in anaerobic, sulfide-rich zones of lakes and lake muds. Purple Phototrophic Bacteria are Gram-negative rods, spirals, ovoid, or bean shaped and some rods are motile via polar flagella. One preferred Purple Phototropic Bacteria for use in this invention are bacteria from the genera *Rhodobacter*, including, *Rhodobacter adriaticus, Rhodobacter blasticus, Rhodobacter capsulatus, Rhodobacter euryhalinus, Rhodobacter indicus, Rhodobacter* sp., *Rhodobacter sphaeroides, Rhodobacter sulfidophilus*, and *Rhodobacter veldkampii*. A particularly preferred bacteria is *Rhodobacter capsulatus*, which has low or no known human toxicity.

Nitrifying Bacteria include bacteria from the genera Nitrobacter and Nitrosomonas. Nitrifying Bacteria are Gram-negative rods, coccoid, spiral, or lobular in shape and may have extensive membrane complexes in cytoplasm.

Sulfur- and Iron-Oxidizing Bacteria include bacteria from the genera Thiobacillus, Beggiatoa, Thioploca, and Thiothrix. Sulfur- and Iron-Oxidizing Bacteria are Gram-negative rods, coccoid, spiral, or lobular shaped and may have extensive membrane complexes in cytoplasm or filamentous with gliding motility.

Hydrogen-Oxidizing Bacteria include bacteria from the genera Alcaligenes. Hydrogen-Oxidizing Bacteria are Gram-negative rods, coccoid, spiral, or lobular shaped and may have extensive membrane complexes in cytoplasm.

Methanotrophs and Methyltrophs include bacteria from the genera Methlyosinus, and Methylcoccus. Methanotrophs and Methyltrophs are Gram-negative motile rods or nonmotile cocci or motile *vibrios* and possess sterols.

*Pseudomonas* and the Pseudomonads include bacteria from the genera *Pseudomonas, Agrobacterium, Rhizobium*, and *Zymomonas. Pseudomonas* and the Pseudomonads are Gram-negative straight or slightly curved rods and are motile via polar flagella.

Acetic Acid Bacteria (Acetobacteraceae) include bacteria from the genera Acetobacter, and Gluconobacter. Acetic Acid Bacteria are Gram-negative straight or curved rods and cocci shaped and are motile via either polar or peritrichous flagella.

Free-Living Aerobic Nitrogen-Fixing Bacteria include bacteria from the genera, Azotobacter, and Azomonas. Free-Living Aerobic Nitrogen-Fixing Bacteria are Gram-negative, large, rod to pear-shaped.

*Neisseria, Chromobacterium*, and Relatives include bacteria from the genera *Neisseria*, and *Chromobacterium. Neisseria, Chromobacterium*, and Relatives are Gram-negative cocci or rod-coccoid shaped and are generally nonmotile or possess "twitching" motility.

Enteric Bacteria include bacteria from the genera *Escherichia, Salmonella, Proteus*, and *Enterobacter*. Enteric Bacteria are Gram-negative, straight rods and are nonmotile to motile via peritrichous flagella.

*Vibrio* and *Photobacterium* include bacteria from the genera *Vibrio*, and *Photobacterium. Vibrio* and *Photobacterium* are Gram-negative curved rods are nonmotile to motile via peritrichous or polar flagella.

*Rickettsias* include bacteria from the genera *Coxiella, Rickettsia,* and *Rochalimaea. Rickettsias* are Gram-negative rod, coccoid, or pleomorphic shaped and are nonmotile.

*Spirilla* include bacteria from the genera *Spirilum, Bdellovibrio,* and *Campylobacter. Spirilla* are Gram-negative are helical to vibrioid shaped are motile via flagella or nonmotile.

Sheathed Proteobacteria include bacteria from the genera Sphaerotilus, and Leptothrix. Sheathed Proteobacteria are Gram-negative are filamentous are generally motile by subpolar flagella while some are nonmotile.

Budding and Prosthecate/Stalked Bacteria include bacteria from the genera Hyphomicrobium, and Caulobacter. Budding and Prosthecate/Stalked Bacteria are Gram-negative rods and are mobile by flagella.

Gliding Myxoacteria include bacteria from the genera Myxococcus, and Stigmatella. Gliding Myxoacteria are Gram-negative rods with gliding motility and production of fruiting bodies which contain myxospores.

Sulfate- and Sulfur-Reducing Bacteria include bacteria from the genera Desulfovibrio, Desulfobacter, and Desulfuromonas. Sulfate- and Sulfur-Reducing Bacteria are Gram-negative straight, curved, or helical rod shaped.

Other insect pathogens or toxins such as that of *Bacillus thuringiensis,* for example, may be utilized for certain insects. *B. thuringiensis* is a Gram positive soil bacteria that has been found to produce insecticidal toxins called Bt toxins. The purified or transgenically expressed Bt toxins are commonly used as insecticides in agriculture. Therefore, the present invention may further comprise other bacterial insecticides for insects, particularly fire ants, or other materials having negative effects on insect populations.

Preliminary results affirm that the microorginisms to be included in the bait should be viable, although essentially dry.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. For example, numerous carbohydrate-rich particulate baits may be used so long as they are regarded as food and retrieved by ants to the colony for ingestion. It is believed that any Gram negative bacteria, particularly of the genera described herein are useable as bacterial insecticides.

Also, other microbial agents may also be substituted for the particular bacteria exemplified. *Pseudomonas aeruginosa, Enterobacter agglomerans, Enterobacter aerogenes*, and *Serratia marcescens* are all Gram negative bacteria. Gram negative bacteria are divided into several classifications. *E. agglomerans* and *S. marcescens* are both members of the family Enterobacteriaceae. *P. aeruginosa* is a member of the family Pseudomonadaceae. Other types of bacteria, including other Gram negative or even Gram positive bacteria that are bacterial insecticides, may be used in the present invention. Although the bacterial strains used in the illustrative embodiments were generally obtained from water effluent of grease traps it is believed that a laboratory strain of *Pseudomonas aeruginosa* or other organisms obtained from another source also demonstrate insecticidal activity against fire ant and the other insects. Therefore effective bacterial strains are not limited to those obtained from grease traps.

EXPERIMENTAL SECTION

EXAMPLE 1

Six strains of bacteria (one of *Pseudomonas aeruginosa*, one of *Enterobacter aerogenes* one of *Enterobacter agglomerans*, and three of *Serratia marcescens*) were isolated from the effluent of a commercial grease trap and are available from BioStim, L.L.C. These strains were grown individually, in 1 liter quantities of Trypticase Soy Broth (Difco) for 18–24 hours, with a final yield of 109–1012 bacteria/mL. The bacteria were removed from the Trypticase Soy Broth by centrifugation at 10,000× g for 20–30 minutes. The bacteria were then resuspended in 100 ml of 10% skim milk (Difco) and, when mixing the strains, all six bacterial strains were mixed together in equal proportions. Dry Quaker Oat Bran was added at 453 g/l liter of original Trypticase Soy Broth medium. The material was mixed to cookie dough consistency and lyophilized until dry. Following lyophilization, the dry material was weighed and ready for use. Approximately 2.5–5.0 g were applied to each fire ant mound in the subsequent Examples unless stated otherwise. As little as 1 g was found to often have similar results.

EXAMPLE 2

A field test was conducted by David L. Johnson on fire ant mounds located on property next to the office of BioStim L.L.C., San Antonio, Tex. in May 1997. The results were 100% kill of the mounds within two weeks (including queens and larva). The 2nd tests were conducted in Mr. Johnson's back yard during the month of June, 1997 at his residence in San Antonio. Mr. Johnson applied the formulation to 10 separate fire ant mounds and there was 100% kill within two weeks. Mr. Johnson conducted a 3rd round of tests in July 1997 in which he baited 3 of five mounds in his front yard in close proximity to two other satellite mounds. The 3rd set of tests resulted in a complete kill in two weeks of the three original mounds and a corresponding kill of the satellite mounds in week three. Dr. Stephen J. Mattingly conducted tests on his personal property on seven mounds in August, 1997 and reported all mounds free of living fire ants in two weeks. A fourth set of tests was conducted on seven mounds located on residential property in August, 1997. All mounds were found to be free of live fire ants within two weeks.

EXAMPLE 3

The oat bran-dried milk-*Pseudomonas, Enterobacter, Serratia*-containing particulate mixture of the present invention has been noted as eliminating or decreasing cockroach populations. With appropriate bait or flavoring, target insects may include, among others, carpenter ants, cockroaches, termites and fire ants of any variety. Termite bait of course would preferably involve a cellulosic material. Carpenter ants may be baited more properly by a particulate mixture comprising, for example, substances such as peanut extract (peanut butter or the like). An important aspect of the present invention is including an appropriate pathogen. The pathogen is preferably slow-acting, not killing the insects immediately. It is believed that, because of fire ants' preference for dietary carbohydrate, a variety of toxins or bacteria pathogenic to fire ants may be included in a particulate mixture and applied to fire ant mounds effectively. When the fire ants retrieve the carbohydrate-rich particles to the colony for ingestion, the toxin or pathogen may have effects in the insect population. Choices of carbohydrate-rich material attractive to fire ants are widely available. Particular toxins or pathogens may be readily tested by the techniques described herein and effective materials identified. Those of skill in the art will understand how the basic successful fire ant control technique may be established. Of great importance is a particulate form attractive to fire ants for consumption. This is most likely to be a material rich in carbohydrates. In addition, the pathogen or toxin should not be readily detectable by the ants and preferably is slow-acting.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention is defined by the appended claims.

EXAMPLE 4

Further experiments to determine the insecticidal activity of the insect bait of the present invention were conducted using ants colonies with 8–12 in. mounds and enclosed in one gallon glass containers. The ambient conditions were uniformly dry with temperatures ranging from 60–75° F. Approximate number of ants, and fire ant activity when slightly disturbed, were observed upon application of the samples, and weekly thereafter. The results are shown in Table 1. Treatment Packets 1 through 6 contained individual bacterial strains while Packet 7 contained a combination of all six strains in one packet. Packet 1 contained a first isolated strain of *Serratia marcescens*; packet 2 the isolated strain of *Enterobacter agglomerans*; packet 3 a second isolated strain of *Serratia marcescens*, 'packet 4, an isolated strain of *Pseudomonas aeruginosa*,' packet 5, an isolated strain of *Enterobacter aerogenes*; packet 6, a third isolated strain of *Serratia marcescens*. The packets were prepared by a procedure similar to that described above. Packet 7 is a formula currently marketed by BioStim, L.L.C. for treatment of grease traps and drain lines. Packets containing 5 gram quantities were found to be effective for killing ants while I gram packets were found to be ineffective indicating that the efficacy of the bait may be dose dependent. When applied in the 5 gram quantities, all formulations resulted in complete kill of the tested ant colony within 2 to 4 weeks. When no fire ant activity was observed upon disturbance of the mound, the soil was checked for live ants and discarded if none were found. This result is indicated in Table 1 by the description "all dead" for approximate number of ants observed.

TABLE 1

| | Approximate Number of Fire Ants/Activity Level | | | | | | | |
|---|---|---|---|---|---|---|---|---|
| Treatment | Initial | Week 1 | Week 2 | Week 3 | Week 4 | Week 5 | Week 6 | Week 7 |
| Control | >100 | >50 | >50 | >50 | >50 | >50 | >50 | >50 |
| (untreated) | high | mod | mod | mod | mod | mod | mod | mod |
| Packet 7 | >100 | >100 | >100 | >100 | all dead | | | |
| (5 gram) | high | low | low | low | none | | | |
| Packet 6 | >100 | <20 | <20 | all dead | | | | |
| (5 gram) | high | low | none | none | | | | |
| Packet 4 | >100 | >50 | >50 | all dead | | | | |
| (5 gram) | high | low | low | none | | | | |
| Packet 2 | >100 | >50 | all dead | | | | | |
| (5 gram) | high | low | none | | | | | |
| Packet 5 | >100 | >50 | <20 | all dead | | | | |
| (5 gram) | high | mod | mod | none | | | | |
| Packet 3 | >100 | >50 | <20 | all dead | | | | |
| (5 gram) | high | low | ND | none | | | | |
| Packet 1 | >100 | >50 | few | all dead | | | | |
| (5 gram) | high | mod | low | none | | | | |
| Packet 4 | >100 | >100 | >50 | >50 | | | | |
| (1 gram) | high | high | mod | high | | | | |
| Packet 7 | >100 | >100 | >50 | >100 | | | | |
| (1 gram) | high | high | mod | high | | | | |

EXAMPLE 5

Preliminary Report on Initial Field Trial of BioStim Microbial Fire Ant Bait

Materials and Methods

The test site was a non-bearing pecan orchard located in eastern Burelson County in the Brazos River flood plain. Fire ants were most likely of the multiple-queen type at a density averaging nearly 430 mounds per acre. Trees within the orchard were on a 45-foot spacing. Plots consisted of an area bounded by three inter-tree spaces, i.e., 135 feet, on a side, or 0.42 acres. The central 45×45 foot square was used as the sample area to allow an ample treated buffer. All active fire ant mounds within the sample area were counted. A 45 foot buffer was left untreated around all sides of all plots.

Initial mound controls were made on the morning of Jul. 24, 1998. A mound was considered active if a dozen or so ants rushed to the surface upon light disturbance with a pointed tool handle. The mounds counts were arrayed from highest to lowest and divided into four equal groups (replications). Treatments were assigned within replications so that the total number of active mounds for each treatment were as equal as possible. Treatments included:

The BioStim bait was prepared as follows: Six Strains are grown separately in 3 liters each of Tryptic Soy Broth (Difco) overnight at 35° C. The cells are separated by centrifugation and suspended in 1 liter of 10% skim milk. The mixture is then added along with 1 liter of Thioglycollate Broth without indicator (Difco) to 1500 grams of dry Quaker Oat Bran and mixed to cookie dough consistency. The material is then lyophilized to dryness, mixed to break up clumps in a food mixer, and packaged for use. Application was made after 5:30 p.m, on 27 Jul. 1998. Evaluations were made on 3, 10, 17 and 25 Aug. 1998 by counting all active mounds within each plot's sample area, as described above. The treatment/rate and method are shown in Table 2.

TABLE 2

| Treatment | Rate | Method |
| --- | --- | --- |
| 1) untreated control | | |
| 2) Logic @ (1% fenoxycarb) | 1.5 lbs/acre | broadcast |
| 3) BioStim Bait | 1.5 lbs./acre | broadcast |
| 4) BioStim Bait | 4.5 lb./acre (equiv.) | placed in center of sample area |

Results

Foraging ants were very attracted to the BioStim product and began carrying it off almost as it hit the ground. It appeared to somewhat more attractive than Logic, though both baits were readily retrieved by the ants. Results of post-treatment counts are shown in Table 3:

TABLE 3

Mean Number of Active Mounds per Plot (4 Replications)

| Treatment | pre-count | 1 wk | 2 wk | 3 wk | 4 wk |
| --- | --- | --- | --- | --- | --- |
| Untreated | 20.25 a | 19.75 a | 23.75 a | 18.50 a | 17.50 a |
| Logic | 20.25 a | 20.00 a | 16.75 a | 12.50 a | 16.00 a |
| BioStim, broadcast | 20.00 a | 16.50 ab | 14.50 b | 11.75 a | 19.50 a |
| BioStim, central | 20.00 a | 13.00 b | 13.00 b | 9.00 a | 18.00 a |
| F | 46.03 (replct) | 10.72 | 11.86 | 1.70 | 3.20 |
| P | 0.0001 | 0.0012 | 0.0008 | 0.2270 | 0.0573 |
| $R^2$ | 0.9684 | 0.8773 | 0.8877 | 0.5315 | 0.6811 |

Means in the same column followed by different letters are significantly different (P<0.05) using PC SAS ANOV A procedures. Means separated using Duncan's multiple range test.

The BioStim product resulted in a fairly rapid reduction in active mound numbers that also appears to be rate-related. Activity then appears to have leveled off. Active mound numbers are significantly lower (P<0.05) for the centrally-placed BioStim product versus untreated and Logic plots at one wk post-treatment. All treatments are significantly lower than untreated plots at two wk, but all treatments are statistically similar after that point.

Weather during the test was extremely hot and, initially, extremely dry. Two significant rain events occurred during the evaluation period that likely caused untreated-plot mound numbers to fluctuate. The fast initial drop in colony numbers in the central-placement plots indicates a potential rate response. In which case future tests should included treatments in a range of five to 20 pounds per acre, for instance. The product is extremely attractive to ants, regardless of its efficacy.

EXAMPLE 6

The example illustrates a procedure for producing a *Rhodobacter capsulatus* based Fire Ant Bait A *Rhodobacter capsulatus* stock culture was prepared in 50% BHI (Brain Heart Infusion) and 50% Glycerol and kept in a freezer at −80° C. The *Rhodobacter* stock culture was streaked onto a yeast agar plate and incubated for 48 to 72 hours at 37° C. in a candle jar.

A *Rhodobacter* medium comprising 90% of a Defined Medium and 10% of Thioglycollate Medium. The Defined Medium included the components set forth in Table 4.

TABLE 4

Defined Medium Composition

| Component | Amount per Liter of Medium |
| --- | --- |
| Fructose or glucose | 4.0 g |
| $(NH_4)_2SO_4$ | 1.0 g |
| $K_2HPO_4$ | 0.9 g |
| $KH_2PO_4$ | 0.6 g |
| $MgSO_4\ 7H_2O$ | 0.2 g |
| $CaCl_2\ 2H_2O$ | 0.075 g |
| EDTA | 0.02 g |
| $FeSO_4\ 7H_2O$ | 0.012 g |
| Thiamine | 1.0 mg |
| Biotin | 0.015 mg |
| Trace element solution | 1.0 ml |

The above components were added to distilled/deionized water in a 1 L volumetric flask. The final volume was brought to 1 L with the addition of distilled/deionized water. The pH of the medium was adjusted (if necessary) to pH 6.8. The medium was then mixed thoroughly and filtered sterilize into sterile culture vessel.

The Trace Elements solution included the components set forth in Table 5.

TABLE 5

Trace Elements Solution Composition

| Component | Amount per 250 mL of Solution |
| --- | --- |
| $H_3BO_3$ | 0.7 g |
| $MnSO_4\ H_2O$ | 0.4 g |
| $Na_2MoO_4\ 2H_2O$ | 0.19 g |
| $ZnSO_4\ 7H_2O$ | 0.06 g |
| $CoCl_2\ 6H_2O$ | 0.05 g |
| $Cu(NO_3)_2\ 3H_2O$ | 0.01 g |

The trace elements solution was prepared by adding the above listed components to distilled/deionized water in a volumetric flask. The final volume was brought to 250 mL with the addition of distilled/deionized water. The solution was then mixed thoroughly.

The *Rhodobacter* Medium was prepared by adding 90% by volume of the Defined Media and 10% by volume of autoclaved Thioglycollate medium in a culture vessel of desired size. The *Rhodobacter* Medium was incubated for 18–24 hours at room temperature (RT) and checked for contamination.

During this *Rhodobacter* Medium test period, a 500 mL starter culture of the *Rhodobacter* at the desired final medium concentration was prepared and incubated at 32° C. in a shaking incubator for 18 to 24 hours.

A sample of the starter culture and the medium in the culture vessel were Gram stained to check for contamination. If no contamination was evident, then the starter culture was added to the culture vessel and incubated at RT with aeration for 48 to 72 hours.

After incubation, a sample of the medium was Gram stained to check for any contamination. If no contamination was evident, then the bacteria was collected by centrifugation at 8K for 10 minutes at 4° C.

The centrifugate, comprising bacterial cells, was resuspended in 10% skim milk. The resuspended bacterial broth was added to oat bran to produce a mixtures of 1 lb of oat bran per 500 mL of original culture volume. Sterile thioglycollate medium can be added to the mixture to obtain a desired consistency, which is preferably a cookie dough like consistency, to form a crude bait. The crude bait was then frozen and lyophilized. After drying, the dried bait was ground to a fine powder and bagged.

The Yeast Agar (Van Niel's Yeast Agar) included the components set forth in Table 6.

TABLE 6

Yeast Agar Composition

| Component | Amount |
|---|---|
| K2HPO4 | 1.0 g |
| MgSO4 | 0.5 g |
| Yeast Extract | 10.0 g |
| Agar | 20.0 g |
| Tap Water | 1.0 L |

The components were added to the tap water and the pH was adjusted to 7.0 to 7.2 and the agar was throughly mixed and poured into agar plates.

EXAMPLE 7

This example illustrates preliminary testing of *Rhodobacter capsulatus* Bait on imported fire ant mounds in San Antonio and Granite Shoals, Tex. during an 18 Month Period (2000–2001).

Estimated Percent Killing by Weekly Applications of2–4 Tablespoons of Biostim nonviable *Rhodobacter capsulatus* Bait of >200 Red Imported Fire Ant Mounds of Varying Sizes in Residential Locations in San Antonio, Tex. and Granite Shoals, Tex. during an 18 Month Period (2000–2001) with Approximate Temperature Ranges of about 70 to 100° F.

TABLE 6

Preliminary Test Results for *Rhodobacter capsulatus* Bait

| Mound Diameter (inches) | One Week | Two Weeks | Three Weeks | Four Weeks | >Four Weeks |
|---|---|---|---|---|---|
| 3 | 70 | 30 | — | — | — |
| 4–6 | 40 | 30 | 20 | 5 | 5 |
| 7–12 | 20 | 30 | 40 | 5 | 5 |
| >12 | 10 | 20 | 30 | 30 | 10 |

The data indicate that when applied to small mounds, the bait is very effective, with all mounds dead within three weeks. As the mound size gets larger, the number of mounds that die in a given period of time decreases more slowly. Thus, the *Rhodobacter capsulatus* bait is effective against fire ants, even though the bacteria itself is non-viable when the bait is applied.

EXAMPLE 8

Individual red imported fire ant mound treatments are evaluated in a trial with a minimum of three treatments: (1) treated with the *Rhodobacter* bait of this invention; (2) untreated control—an untreated area is monitored for fire ant activity; and (3) a "standard" treatment using a product/method similar to the one being evaluated.

Plots are established to provide four replications of these three treatments for purposes of statistical analysis (randomized complete block design). The mounds is established on plots in a line that are of a standard width (e.g., 30 ft) but vary in length so that each plot contains 10 active red imported fire ant mounds (this method is informally called the "railroad track" design). The size of the mounds is determined. If more than one line of plots is to be established because of space limitations, the plots are set at least 20 ft apart. If treatments can cause effects in neighboring colonies (which is often the case for some types of bait-formulated products), untreated "buffer" areas can be left between plots in each line.

Once plots (a minimum of 12) are established, they are numbered consecutively and plots are listed (arrayed) in order from the longest to shortest plot length. This sequence of plot numbers is then divided into four "blocks" (replicates), each containing the number of treatments in the trial (a minimum of three). In this way, there is a "replicate" block of long plots, one containing short plots and two with intermediate length plots. This technique is used to assure that treatment is applied to a set of plots that have the same probability of having migrating fire ant colonies entering or leaving the treatment areas. Treatments are assigned within blocks so that total plot lengths for all 4 blocks for each treatment are as equivalent as possible to doubly assure equal invasion pressure.

Fire ant mound activity is monitored using the "minimal disturbance method" whereby a mound is slightly disturbed with a stick. If a large number (25 or more) of worker ants emerge from the disturbed mound in a defensive manner to protect it, the colony in the mound is assumed to be active. Mounds with less than 25 worker ants will continue to be monitored on a weekly basis to determine if complete eradication has occurred. This evaluation is made before and periodically following application of treatment(s). Exact post-treatment times will be scheduled to best compare the experimental product(s) speed of action relative to untreated and "standard" treatments (e.g. for fast-acting ingredients, post-treatment evaluations are made 7, 14, 21 and 28 days after treatment).

Occasionally, ant colonies move away from treated areas, or a colony may split into several colonies. These are called "satellite mounds". At least on the last post-treatment evaluation date, plots are examined for the presence of these "new" mounds found in locations not originally treated and marked.

Results of ant mound monitoring efforts are analyzed using PC-SAS analysis of variance (ANOVA) and means (averages) are separated using Tukey's Studentized range test.

Description of Monitoring Protocol

In one set of experiments, approximately 2–4 tablespoons of bait or enough to completely cover the entire fire ant mound is applied. After seven days, if the mound is still active, a second application is made. A third application in three weeks is made, if necessary. Final monitoring of fire ant mounds is at 28 days.

In a second set of experiments, water is applied to thoroughly soak the mound before each application. This is repeated at weeks 1, 2, and 3 as necessary.

Controls will be treated in the same manner as the mounds treated with the compositions of this invention.

REFERENCES

The references in the following list are incorporated in pertinent part by reference herein for the reasons cited in the text.

Adams, "Agricultural and medical impact of the imported fire ants," *In: Fire ants and leaf-cutting ants: Biology and management*, C. S. Lofgren and R. K. Vander Meer (eds.), Westview Press, Boulder, Colo., p. 48–57, 1986.

Adams anq Lofgren, "Red imported fire ants [Hymenoptera: Formicidae): Frequency of sting attacks on residents of Sumter County, Ga.," *J Med. Entomol.,* 18:378–382, 1981.

Amdro Fire Ant Insecticide, Produce label, American Cyanamide Co., Wayne, N.J., 1987.

Banks, Lofgren, Williams, "Development of toxic baits for control of imported fire ants," *In: Pesticide formulations and application systems: 4th Symp.*, Special Tech. Publ. 875, Amer. Soc. Test. Mater., Philadelphia, pp. 133–143, 1985.

L. E. Gilbert Laboratory, U. T. Austin, "Using phorid flies in the biocontrol of imported fire ants in Texas," http://uts.cc.utexas.edu/gilbert/research/fireants/fireant.html, 1997.

Lofgren, "The economic importance and control of imported fire ants in the United States," *In: Economic impact and control of social insects*, S. B. Vinson (ed.), Praeger, N.Y. p. 227–256, 1986a.

Logic Fire Ant Bait, Technical Data, Commercial brochure.

Logic Professional Fire Ant Bait, Product Label, Terminix International Inc.

Vander Meer, "The trial pheromone complex of *Sole no psis invita* and *Solenopsis richteri,*" *In: Fire ants and leaf-cutting ants, Biology and management*, C. S. Lofgren and R. K. Vander Meer (eds.), Westview Press, Boulder, Colo., p. 201–210,1986.

Vander Meer et al., "Fire ant phagostimulants," *Florida Entomologist,* 78(1):145–154,1995.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A composition for controlling or eliminating insect populations comprising an insect food and an insecticidal effective amount of a *Rhodobacter capsulatus* bacteria, where the insect food comprises at least 60% carbohydrate and where the insecticidal effective amount is sufficient to reduce or kill an insect population when the composition is ingested by insects in the insect population or taken to a nest for subsequent ingestion by insects in the insect population resulting in insect death after ingestion and where the insects are selected from the group consisting of cockroaches and fire ants.

2. The composition of claim 1, wherein the insecticidal effective amount comprises from about $5 \times 10^9$ to about $1 \times 10^{13}$ bacteria per gram of the composition.

3. The composition of claim 1, wherein the bacteria are viable, non-viable, or mixtures thereof.

4. A insecticidal composition for controlling or eliminating insect populations comprising a treating amount of a bait including an insect food and an insecticidal effective amount of a *Rhodobacter capsulatus* bacteria, where the fire ant food comprises at least 60% carbohydrate and where the treating amount of the bait is sufficient to treat an insect population and where the insecticidal effective amount of the *Rhodobacter capsulatus* bacteria is sufficient to reduce or kill an insect population, when the bait is ingested by insects in the insect population or taken to a nest for subsequent ingestion by insects in the insect populations resulting in insect death after ingestion and where the insects are selected from the group consisting of cockroaches and fire ants.

5. The composition of claim 4, wherein the bacteria are viable, non-viable, or mixtures thereof.

6. The composition of claim 4, wherein the treating amount is about 5 grams of the composition per insect population to be treated.

7. The composition of claim 4, wherein the insecticidal effective amount is from about $5 \times 10^9$ to about $1 \times 10^3$ bacteria per gram of the composition.

8. The composition of claim 4, wherein the treating amount is about 5 grams of the composition per insect population to be treated and the insecticidal effective amount is from about $5 \times 10^9$ to about $1 \times 10^{13}$ bacteria per gram of the composition.

9. A composition for controlling or eliminating fire ant populations comprising a fire ant food and an insecticidal effective amount of a *Rhodobacter capsulatus* bacteria, where the fire ant food comprises at least 60% carbohydrate and where the insecticidal effective amount is sufficient to reduce or kill a fire ant population when the composition is ingested by fire ants in the fire ant population or taken to a nest for subsequent ingestion by the fire ants in the fire ant population resulting in fire ant death after ingestion.

10. The composition of claim 9, wherein the insecticidal effective amount comprises from about $5 \times 10^{13}$ to about $1 \times 10^{13}$ bacteria per gram of the composition.

11. The composition of claim 9, wherein the bacteria are viable, non-viable, or mixtures thereof.

12. The composition of claim 9, wherein the composition comprises dry particles or granules.

13. The composition of claim 9, wherein the composition comprises a fine powder.

14. The composition of claim 9, wherein the carbohydrate comprises a cereal bran.

15. The composition of claim 9, wherein the carbohydrate comprises oat bran.

16. The composition of claim 9, wherein the fire ant food further comprises dried milk.

17. The composition of claim 9, wherein the fire ant food further comprises a residue of a thioglycollate bacterial broth.

* * * * *